United States Patent [19]

Fujishiro et al.

[11] 4,105,524
[45] Aug. 8, 1978

[54] OXYGEN CONCENTRATION SENSOR FOR HEATED GASEOUS MIXTURE

[75] Inventors: Takeshi Fujishiro, Yokohama; Kiyoshi Wazawa, Fujisawa; Takeshi Oguro, Yokosuka, all of Japan

[73] Assignee: Nissan Motor Company, Ltd., Japan

[21] Appl. No.: 742,698

[22] Filed: Nov. 17, 1976

Related U.S. Application Data

[63] Continuation of Ser. No. 559,925, Mar. 19, 1975, abandoned.

[30] Foreign Application Priority Data

Apr. 17, 1974 [JP] Japan .................................. 49/43121

[51] Int. Cl.² .......................................... G01N 27/46
[52] U.S. Cl. ................................................ 204/195 S
[58] Field of Search .......................... 204/195 S, 1 S

[56] References Cited

U.S. PATENT DOCUMENTS

| 2,798,577 | 7/1957 | La Forge | 29/195 M |
|---|---|---|---|
| 2,996,401 | 8/1961 | Welch et al. | 29/195 M |
| 3,216,911 | 11/1965 | Kronenberg | 204/195 S |
| 3,503,809 | 3/1970 | Spacil | 204/195 S |
| 3,661,749 | 5/1972 | Richardson | 204/195 S |
| 3,809,639 | 5/1974 | Faurschou et al. | 204/195 S |
| 3,841,987 | 10/1974 | Friese et al. | 204/195 S |
| 3,847,778 | 11/1974 | Riddel | 204/195 S |

FOREIGN PATENT DOCUMENTS 48,083 6/1966 German Democratic Rep. ... 204/195 S

*Primary Examiner*—T. Tung
*Attorney, Agent, or Firm*—Robert E. Burns; Emmanuel J. Lobato; Bruce L. Adams

[57] ABSTRACT

A sensor mainly intended for use in an engine exhaust system and constituted of a hollow and bottomless cylinder of a solid oxygen-ion electrolyte such as a $ZrO_2$-CaO system. A pair of porous and conductive films are respectively deposited on the outer and inner surfaces of the cylinder and a pair of conductor members are fixed to the cylinder. One of the conductor members covers hermetically one end of the cylinder while the other is fixed to the opposite end region of the cylinder and bored such that the interior space of the cylinder communicates with an exterior atmosphere exclusively through the bore and such that the cylinder can be entirely held in a heated gas subject to the measurement when the sensor is attached to a vessel containing the heated gas therein. The cylinder of solid electrolyte may be made up of either a single piece or a plurality of identical pieces hermetically joined to one another in an axial direction, wherein the conductive films of each piece are connected in series with ones of the adjoining piece.

2 Claims, 4 Drawing Figures

OXYGEN CONCENTRATION SENSOR FOR HEATED GASEOUS MIXTURE

This is a continuation, of application Ser. No. 559,925, filed Mar. 19, 1975, now abandoned.

BACKGROUND OF THE INVENTION

The present invention relates to a device for sensing oxygen concentration in a heated gaseous mixture such as an engine exhaust gas. The device is fundamentally based on a solid oxygen-ion electrolyte concentration cell.

In recent years it has become of great importance to measure oxygen concentrations in exhaust gases from various engines, particularly from automotive internal combustion engines, mainly for the following reason.

In various systems now in practice and/or under development for converting harmful or noxious components of an engine exhaust gas such as unburned hydrocarbons, carbon monoxide and oxides of nitrogen into harmless substances such as water, carbon dioxide and nitrogen, the air-to-fuel ratio of a combustible mixture fed to the engine is frequently an important factor for the operation of such systems. For example, the air-to-fuel ratio must be maintained practically stoichiometric in order to use a new catalyst, which is expected to cause all or part of the above-mentioned harmful substances to undergo catalytic reactions to give the above-mentioned harmless substances at high efficiencies in practical systems. It is known that the air-to-fuel ratio can be estimated from the partial pressure of oxygen in the exhaust gas when the air-to-fuel ratio is around the stoichiometric ratio. When the exhaust gas is subjected to no chemical treatment, the oxygen partial pressure in the exhaust gas is usually of the order of $10^{-2}$ atm for an air-to-fuel ratio higher than the stoichiometric ratio but of the order of $10^{-3}$ atm for an air-to-fuel ratio lower than the stoichiometric. When, however, the exhaust gas is subjected to either an after-burning or catalytic reactions and is in thermodynamically equilibrium states, the oxygen partial pressure exhibits a sharp change at the stoichiometric air-to-fuel ratio of the combustible mixture from a value of the order of $10^{-3}$ atm for an air-rich ratio to a value of the order of $10^{-15}$ to $10^{-30}$ atm for a fuel-rich ratio. Therefore, it is possible to detect whether the air-to-fuel ratio for an engine in operation is maintained at the stoichiometric ratio or deviated therefrom by measuring the oxygen partial pressure in the exhaust gas. A signal representing the measured oxygen partial pressure or the estimated air-to-fuel ratio may be supplied to a control system for controlling, for example, the rate of fuel injection into the engine in order to maintain the air-to-fuel ratio at a predetermined or the stoichiometric ratio thereby to accomplish the modification of the exhaust gas at expected efficiencies.

A typical sensor now in practice for sensing the oxygen partial pressure in a heated gaseous mixture such as an engine exhaust gas is principally based on a concentration cell made of a layer of a solid electrolyte in which oxygen ions function as the electron carriers. The magnitude of the electromotive force in this type of cell is dependent on the ratio of an oxygen partial pressure in an atmosphere communicating with one side of the electrolyte layer and another oxygen partial pressure applied to the other side and determined by the well known Nernst's equation.

In practical applications of this oxygen sensor to engine exhaust systems, the electrolyte layer must be shaped in such a manner that one side thereof is exposed to an exhaust gas flowing in the exhaust system while the other side is exposed to the atmospheric air which is usually used as a reference gas.

SUMMARY OF THE INVENTION

It is therefore an object of the present invention to provide an oxygen concentration sensor of improved configuration, which is principally based on a conventional solid oxygen-ion electrolyte, but simple in construction, easy to fabricate and substantially free from arising of temperature difference in the electrolyte layer thereof during practical uses.

It is another object of the invention to provide an oxygen concentration sensor which comprises a plurality of sets of electrolyte layers whereby the magnitude of the electromotive force of a single device can be increased proportionally to the number of the electrolyte layers.

According to the invention, there is provided a device for sensing differences in oxygen partial pressure between a heated gaseous mixture in a vessel and a reference gas outside the vessel, which divice comprises: a generally circular, hollow and bottomless cylinder made of a solid oxygen-ion electrolyte; first and second porous and conductive films deposited on the outer and inner surfaces of the cylinder, respectively; a first conductive member which is fixed to the cylinder and electrically connected with one of the conductive films and hermetically covers one end of the cylinder; and a second conductive member which is fixed to the cylinder and electrically connected with another of the conductive films. The second conductive member is bored, shaped and arranged such that the interior space of the cylinder communicates with an exterior atmosphere exclusively through a bore in the second conductive member and that the cylinder is entirely held in the vessel when the device is attached to the vessel.

The solid electrolyte cylinder of a device according to the invention may be either a jointless single piece member or an assembly of at least two identical pieces hermetically joined with one another in an axial direction. In the latter case, each of the cylindrical pieces is provided with the first and second conductive films, and the films on each piece are connected in series with ones on the adjoining piece.

Other features and advantages of the invention will be fully understood from the following detailed description of preferred embodiments thereof with reference to the accompanying drawings.

DESCRIPTION OF THE PREFERRED EMBODIMENTS

Figure 1:
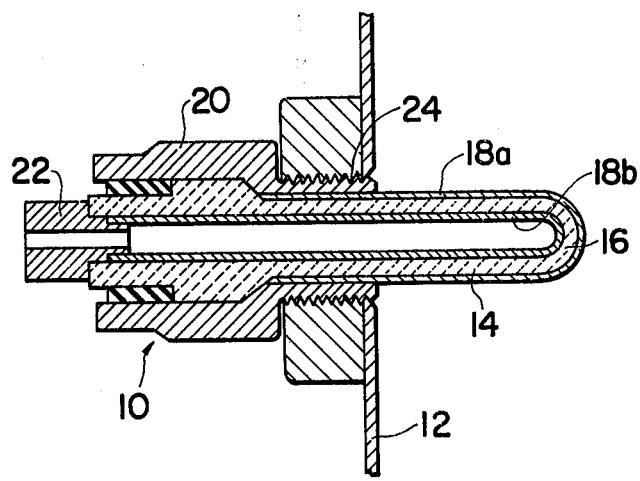
FIG. 1 is a longitudinal sectional view of a conventional oxygen sensor for sensing the oxygen partial pressure in an engine exhaust gas.

Referring to FIG. 1, a prior art oxygen sensor 10 for use in exhaust systems of internal combustion engines is shown in a state associated with an exhaust pipe 12. An essential portion of the oxygen sensor 10 is a layer 14 of a solid oxygen-ion electrolyte, which is shaped generally tubular forming a rounded bottom 16 at one end thereof, and two porous films 18a and 18b of an electrically conductive substance respectively deposited on the outer and inner surfaces of the electrolyte layer 14. The electrolyte layer 14 is usually made of the so-called stabilized zirconia ceramics which is a solid solution of $ZrO_2$ and a stabilizing oxide such as CaO or $Y_2O_3$. The conductive films 18a and 18b are usually formed by applying a paste comprising powdered platinum in an organic binder on the both sides of the electrolyte layer 14 followed by heating to fuse the platinum powder to the electrolyte layer 14. A metal shell 20 covers the electrolyte layer or the tube 14 so as to leave a portion thereof including the bottom 16 exposed and is electrically connected to the exterior platinum film 18a. Another electrode member 22 is connected to the inner film 18b so as to keep the interior of the bottomed tube 14 exposed to an exterior atmosphere.

The thus constructed oxygen sensor 10 is hermetically thread-fitted with a port 24 provided through the wall of the exhaust pipe 12 such that the uncovered portion of the bottomed tube 14 protrudes into the exhaust pipe 12. When the outer platinum film 18a is exposed to an exhaust gas flowing in the exhaust pipe 12 and the inner platinum film 18b is kept in communication with the atmospheric air, which has an oxygen partial pressure of about 0.21 atm, the magnitude of an electromotive force developed between the two electrodes 20 and 22 is dependent on the ratio of 0.21 atm to an oxygen partial pressure in the exhaust gas.

Unfortunately, this type of oxygen sensor 10 has several disadvantages from the practical viewpoint. Firstly, neither productivity nor production cost of the electrolyte layer 14 is satisfactory because of the round-bottomed shape thereof. Secondly, the electrolyte layer 14 is liable to crack and break down due to a considerable temperature difference between the bottom portion, which is necessarily exposed to an exhaust gas temperature of about 400° to 900° C, and the remaining portion in the atmosphere. Besides, the above described configuration of the oxygen sensor 10 makes it practically impossible to use a plurality of the electrolyte layers 14 at a substantially same location for the purpose of increasing the magnitude of the developed electromotive force.

Figure 2:
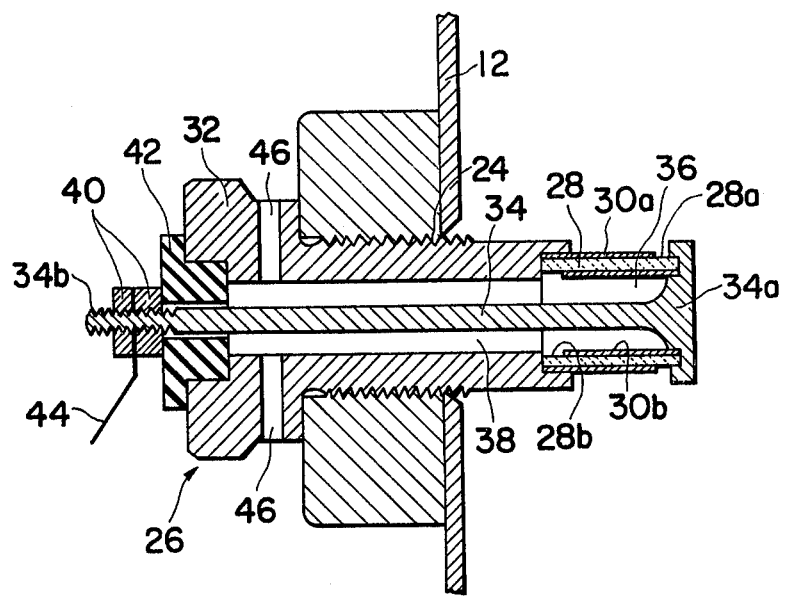
FIG. 2 is a longitudinal sectional view of an oxygen sensor for the same purpose embodying the invention.

In the drawings, FIG. 2, an oxygen sensor 26 as a first preferred embodiment of the invention is shown in association with an exhaust pipe 12 of FIG. 1. A solid oxygen-ion electrolyte layer 28 of this oxygen sensor 26 is shaped cylindrical and bottomless having an annular cross-section. The electrolyte material may be any of known solid electrolyte in which oxygen ions function as the electron carriers. For example, a commercially available stabilized zirconia ceramics which is composed of 85 mole % of $ZrO_2$ and 15 mole % of CaO is an excellent material. The outer and inner peripheral surfaces of the electrolyte cylinder 28 are respectively coated with a pair of porous films 30a and 30b of an electrically conductive substance such as platinum. The outer film 30a is formed such that an annular end region 28a of the outer surface of the electrolyte cylinder 28 is left exposed. The inner film 30b is formed so as to leave an annular end region 28b of the inner surface of the electrolyte cylinder 28 uncovered. The end regions 28a and 28b are located respectively at the opposite end portions of the electrolyte cylinder 28. These films 30a and 30b serve as the electrodes of the concentration cell are identical with the films 18a and 18b of the prior art oxygen sensor 10 of FIG. 1 except for the shape thereof. A hollow metal member 32 is fixed to the electrolyte cylinder 28 in such a manner that an end portion of the cylinder 28, which portion is more remote from the exposed region 28a of the outer surface, is closely inserted into the hollow member 32. The exterior of the hollow member 32 is locally threaded so as to fit with the port 24 of the exhaust pipe 12. The outer conductive film 30a is electrically connected with the hollow member 32, so that the hollow member 32 serves both as a support member and as one of the conductors of the device 26. Another metal member 34 which serves as the other conductor of the device 26 is shaped generally rod-like but has a disc-shaped portion 34a at one end thereof. The disc-shaped portion 34a is fixed to the electrolyte cylinder 28 so as to cover the free end of the cylinder 28 completely, to which end the exposed surface region 28a is contiguous. The inner conductive film 30b is electrically connected with the disc-shaped portion 34a of this conductor member 34. These two conductive members 32 and 34 are made of a corrosion-resistant metal such as a stainless steel or an iron-chromium alloy which has a thermal expansion coefficient close to that of the solid electrolyte 28. The respective joints between the electrolyte cylinder 28 and the conductor members 32 and 34 are hermetically sealed. The rod-like portion of the conductor member 34 extends inwardly of the electrolyte cylinder 28 and the hollow member 32, but comes into no contact with them.

Thus, a major portion of the outer conductive film 30a is exposed and the inner film 30b or the interior space 36 of the cylinder 28 communicates with the atmosphere exclusively through a bore 38 in the hollow member 32.

The rod-end portion 34b of the conductor member 34 protrudes from the hollow member 32 and is preferably threaded so that the conductor member 34 is held in position by means of nuts 40 and a spacer 42 interposed between the nuts 40 and the free end of the hollow member 32. The spacer 42 is made of a non-conductive material such as an aluminum oxide ceramics. A terminal 44 is connected to the nuts 40 for wiring to a control circuit (not shown). A plurality of through holes 46 are formed in the wall of the hollow member 32 at locations between the threaded portion thereof and the spacer 42 to provide fluid communication between the interior space 36 of the cylinder 28 and the atmosphere.

When the thus constructed oxygen concentration sensor 26 is attached to the port 24 of the exhaust pipe 12 as illustrated in FIG. 2, the electrolyte cylinder 28 is entirely held inside the exhaust pipe 12, and the outer surface of the cylinder 28 communicates with an exhaust gas following in the exhaust pipe 12 through the porous outer film 30a. On the other hand, the inner surface of the cylinder 28 is isolated from the exhaust gas but communicates with the atmospheric air through the porous inner film 30b, the space 36, the bore 38 and the holes 46.

The hermetic seals at the respective joints between the electrolyte cylinder 28 and the conductor members 32 and 34 are preferably attained by preliminarily metallizing the surfaces of the electrolyte cylinder 28 locally at regions for joints and thereafter soldering the conductor members 32 and 34 thereto. The surface of the $ZrO_2$-CaO ceramics can be metallized by well known processes. For example, a paste containing a powdered material such as a mixture of Mo, Mn and Ti; W, $MnO_2$ and $TiO_2$; or Mo, $MnO_2$ and $TiO_2$ dispersed in an organic solvent is applied onto the selected regions of the surface. Then the electrolyte cylinder 28 is baked at a temperature of about 1,200° to about 1,600° C in a hydrogen atmosphere containing steam therein to give thin metallic coatings (not shown) on the selected regions of the surface. The adhesion strength of the thus formed coatings can be enhanced by fabricating the electrolyte cylinder 28 from a solid electrolyte material which contains other than $ZrO_2$ and CaO a minor amount, e.g. about 3% by weight, of $SiO_2$ and/or $Al_2O_3$. These minor amounts of oxides are present in the resulting ceramics as a secondary phase distinct from the solid solution phase of $ZrO_2$-CaO and exhibit strong affinity for the above metallic coatings. In this case the above described paste is preferably admixed with small amounts of powdered $ZrO_2$ and/or $SiO_2$.

The thus metallized regions are then plated, e.g., with nickel and also the mating regions of the conductor members 32 and 34 are plated similarly. Finally the conductor members 32 and 34 are joined with the electrolyte cylinder 28 at the plated regions by means of a silver-copper or gold-copper solder.

It will be apparent that the electrolyte cylinder 28 may be turned 180° from the position illustrated in FIG. 2, so that the outer and inner conductive films 30a and 30b are connected with the disc-shaped portion 34a and the hollow member 32 respectively reversely to the above description.

As seen from the above description and the illustration in FIG. 2, the oxygen concentration sensor 26 according to the invention can be fabricated by a series of steps, each of which is comparatively simple and can be carried out stably on industrial scales. It is particularly advantageous that uniformity in the quality of the electrolyte cylinder 28 is easily attained together with reduction in the production cost due to the bottomless cylindrical shape and that a reliable electrical connection between the inner conductive film 30b and the conductor member 34 can be attained easily.

This oxygen concentration sensor 26 is used in the same way as the prior art sensor 10 of FIG. 1 and develops the same magnitude of electromotive force. Since the solid electrolyte 28 is kept entirely in the exhaust pipe 12, the afore-mentioned fragility of the prior art sensor 10 resulting from an disadvantageous temperature distribution is completely eliminated from the sensor 26 of the invention.

Figure 3:
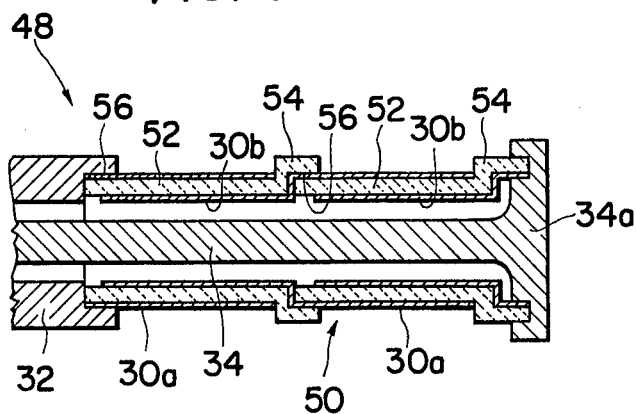
FIG. 3 is a fragmentary longitudinal sectional view of another oxygen sensor as a second embodiment of the invention, in which two sets of concentration cells for the sensor of FIG. 2 are assembled in series.
Figure 4:
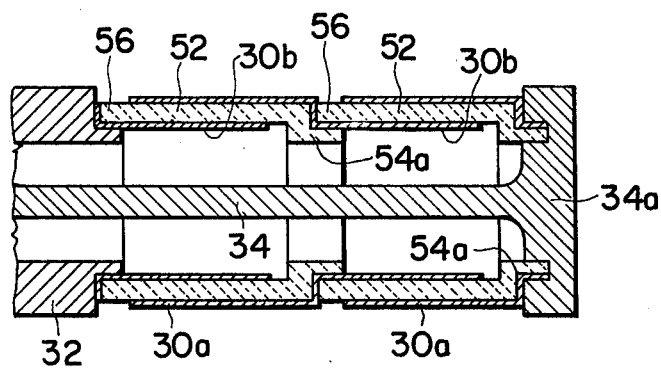
FIG. 4 is a generally similar view to FIG. 3, but shows a slight modification in a local shape of the cells for connection with each other.

Another advantage of the invention from a different point of view will be described with reference to FIGS. 3 and 4. In FIG. 3, an oxygen concentration sensor 48 as another preferred embodiment of the invention is shown fragmentally. In this sensor 48, the cylindrical solid electrolyte 50 is not a jointless one-piece member as the cylinder 28 of the sensor 26 in FIG. 2 but an assembly of two pieces of identical cylinders 52 which are joined axially with each other. These cylinders 52 have an annular cross section and no bottom. The two pieces of cylinders 52 may be butt-joined with each other, but it is more practicable to make an end region 54 of each cylinder 52 stepped so as to fit with the opposite straight end 56 thereof as illustrated in FIG. 3. Each cylinder 52 is provided with the outer and inner conductive films 30a and 30b. The inner film 30b is formed so as to cover the inner surface of the stepped region 54 and connected with the outer film 30a on the other piece of cylinder 52. The joint between the two cylinders 52 is hermetically sealed by the above described procedures of metallizing, plating and soldering. In other respects, this sensor 48 is constructed identically with the sensor 26 of FIG. 2.

It will be apparent that the magnitude of the electromotive force of this sensor 48 is twice the one of the sensor 26 of FIG. 2 for the same oxygen partial pressure since two sets of the same concentration cells are connected in series. It will be understood that the number of the electrolyte cylinders 52 can be increased to three or more if necessary. Thus, the configuration of an oxygen concentration sensor 48 according to the invention brings about an increased magnitude of electromotive force neither using any extra means nor increasing the number of the sensors.

The stepped region 54 of the electrolyte cylinder 52 is not necessarily enlarged in diameter as illustrated in FIG. 3. As shown in FIG. 4, an end region 54a of each cylinder 52 may be stepped to become smaller in diameter and fittable with the inner surface of the straight end 56 of the other piece of cylinder 52. In this modification, the outer surface of the stepped region 54a is covered with the outer conductive film 30a. This modification does not affect the performance of the sensor 48, so that whichever configuration of FIG. 3 or FIG. 4 may be employed simply considering the degree of convenience in production.

What is claimed is:

1. A device for sensing differences in oxygen partial pressure between a heated gaseous mixture in a vessel and a reference gas outside the vessel, the device comprising:

(a) an assembly of two identically shaped solid electrolyte oxygen concentration cells, each of said cells having an open-ended tubular body of a solid oxygen-ion electrolyte ceramic composed of $ZrO_2$ and CaO, said body having a straight major portion including one end thereof and a cross-sectionally smaller minor end portion which also is straight and includes the other end of the tubular body, and two porous and electrically conductive films of platinum deposited respectively on the outer and inner surfaces of said tubular body, the outside of said minor portion being entirely covered with the outer conductive film, said cells being joined axially and hermetically with each other such that said minor portion of said tubular body fits into the inside of said major portion of an adjacent tubular body and that the outer conductive film is joined with the inner conductive film of the adjacent cell at each joint between two adjacent cells to give a series electrical connection, so that said assembly has generally the shape of a hollow and straight cylinder which is open at both ends;

(b) a first conductor member fixed to said cylinder to hermetically close one end of said cylinder and electrically connected with a first one of said two conductive films of one of said cells providing said one end of said cylinder, said first conductor member having a rod-shaped portion extending axially through said cylinder;

(c) a second conductor member hermetically fixed to one of said cells providing the other end of said cylinder and electrically connected with a second one of said two conductive films of the cell providing said other end, said second conductor member having a bore exclusively providing communication between the interior space of said cylinder and an exterior atmosphere and allowing said rod-shaped portion of said first conductor member to pass therethrough;

said first conductor member and said second conductor member being made of a corrosion-resistant metal which has a thermal coefficient close to the thermal expansion coefficient of said solid electrolyte and selected from stainless steels and iron-chromium alloys; and said cylinder being disposed in use entirely in said vessel.

2. A device according to claim 1, including a solder joint joining said cylinder with said first and second conductor members, said solder joint comprising a metallizing coating formed on the surface of said tubular body, a first metal coating plated on said metallizing coating, a second metal coating plated on the surface of each of said first and second conductor members and a solder layer interposed between the plated metal coatings.

* * * * *